United States Patent

Laruelle

[11] Patent Number: 5,827,536
[45] Date of Patent: Oct. 27, 1998

[54] PHARMACEUTICAL DOSAGE FORMULATIONS OF FENOFIBRATE AND THEIR APPLICATIONS

[75] Inventor: Claude Laruelle, Villeneuve Loubet, France

[73] Assignee: CLL Pharma, Nice, France

[21] Appl. No.: 672,852

[22] Filed: Jul. 25, 1996

[30] Foreign Application Priority Data

Jul. 27, 1995 [FR] France .................................. 95 09142

[51] Int. Cl.⁶ ..................................................... A61K 9/48
[52] U.S. Cl. ........................ 424/451; 424/455; 424/456; 514/962; 514/975
[58] Field of Search .................. 424/451, 452, 424/455, 456; 514/975

[56] References Cited

FOREIGN PATENT DOCUMENTS

| | | |
|---|---|---|
| 0256933 | 2/1988 | European Pat. Off. . |
| 0330532 | 8/1989 | European Pat. Off. . |
| 2617047 | 6/1987 | France . |
| WO82/01649 | 5/1982 | WIPO . |

OTHER PUBLICATIONS

Chemical Abstracts, vol. 112, No. 8, Feb. 19, 1990 & 5th Congr. Int. Technol. Pharm., vol. 3, 1989, pp. 190–199. A. Ben–Amor et al., "Augmentation of the Bioavailability of a Hypolipemic Agent for Incorporation into a Liquid–Containing Gel".

Primary Examiner—Thurman K. Page
Assistant Examiner—James M. Spear
Attorney, Agent, or Firm—Lowe Hauptman Gopstein Gilman & Berner

[57] ABSTRACT

Soluble fenofibrate (Rec. INN) formulations exhibiting a significantly improved bioavailability after oral administration ("superbioavailability"), a process for their production and medicaments comprising these formulations. The said fenofibrate pharmaceutical dosage formulations essentially contain fenofibrate in solution in a solubilizing agent consisting of a non-ionic surfactant, diethylene glycol monoethyl ether (DGME).

12 Claims, 1 Drawing Sheet

PHARMACEUTICAL DOSAGE FORMULATIONS OF FENOFIBRATE AND THEIR APPLICATIONS

The present invention relates to soluble fenofibrate (Rec. INN=Recommended International Non-proprietary Name) formulations exhibiting a significantly improved bioavailability after oral administration ("superbioavailability"), to a process for their production and to medicaments comprising these formulations.

Fenofibrate is a substance which has been used for more than 20 years in most countries of the world for the treatment of endogenous hyperlipidaemias, hypercholesterolaemias and hypertriglyceridaemias in adults. Prolonged treatment with fenofibrate at the rate of 300 to 400 mg per day makes it possible to obtain a reduction in total cholesterol of 20 to 25% and a reduction in the levels of triglycerides of 40 to 50%. It thus opposes the development of atherosclerosis.

This clinical activity is the result of the pharmacological effect due to the reduction in the low density atherogenic fractions (VLDL and LDL cholesterol). This pharmacological effect is reflected by:

an improvement in the distribution of plasma cholesterol, the ratio of total cholesterol to HDL cholesterol being reduced, an average decrease in uricaemia of the order of 25%, a platelet anticoagulant effect.

Fenofibrate was initially introduced onto the market in France in 1975 under the trade name Lipanthyl in the form of gelatin capsules containing a dose of 100 mg of active principle, according to the formula:

| fenofibrate | 100 mg |
|---|---|
| excipients | q.s. for 250 mg for one gelatin capsule. |

The usual posology was from 3 to 4 gelatin capsules per day, taken on 3 or 4 occasions, i.e. 300 to 400 mg of active principle per day.

According to Drouin et al. [Current Therapeutic Research, 1979, 26, 3, 357–362], the hypocholesterolaemic effect of fenofibrate is demonstrated with plasma levels of the circulating metabolite, fenofibric acid, ranging from less than 5 $\mu$g/ml up to 35 $\mu$g/ml. It is desirable that the circulating levels should not exceed 10 $\mu$g/ml.

Inasmuch as cases of hepatic attack, digestive and intestinal disorders and bile lithiasis formations have been reported, it is highly desirable to reduce the dose of fenofibrate ingested daily to the active minimum thereof.

Finally, Drouin reports that when patients do not respond to the pharmacological effects of fenofibrate, this is due to poor absorption of the medicament administered.

A substantial advance was, in particular, the development by the Inventor of a formulation containing 250 mg, which makes it possible to take a single daily dose, according to the formula:

| fenofibrate | 250 mg |
|---|---|
| excipients | q.s. for 360 mg for one gelatin capsule |

This formulation was the subject of French Patent No. 2,494,112, filed in 1980.

European Patent No. 256,933, filed in 1987, on behalf of Ethypharm describes a medicament in the form of fenofibrate-based microgranules, each granule containing a neutral core, a fenofibrate-based layer and a protective layer; fenofibrate is present in the fenofibrate-based layer in the form of crystalline microparticles with a size less than or equal to 50 $\mu$m and preferably of the order of 10 $\mu$m.

Such a pharmaceutical dosage form promotes, in particular, the absorption of fenofibrate in the digestive tract.

French Patent No. 2,627,696, filed in 1988, on behalf of Fournier Innovation et Synergie, relates to a new pharmaceutical dosage form of fenofibrate which contains fenofibrate comicronized with a solid surface-active agent. It also relates to the process for the preparation of this pharmaceutical dosage form and to its use in improving in vivo bioavailability.

This new pharmaceutical dosage form is sold under the trade name Lipanthyl 200®. It represents a major advance since the daily posology, which was from 300 to 400 mg per day taken on 3 or 4 occasions, changed successively to 250 mg per day, taken once, and then to 200 mg per day, taken once.

Consequently, the Inventor has set himself the aim of providing a fenofibrate-based pharmaceutical dosage form in the form of a solution which makes possible the oral administration of a daily dose of fenofibrate of less than 200 mg, while increasing the intestinal absorption of the fenofibrate (superbioavailability).

In a first study, Brodie et al. [Arzneimittel Forschung, 1976, 26, 5, 896–901] have shown that dissolving fenofibrate in sunflower oil makes it possible to obtain virtually complete intestinal resorption whereas, when the product is administered in solid form in a gelatin capsule, the circulating active metabolite, fenofibric acid, is only found in the urine in the proportion of 28% when administration is carried out while fasting: Desager et al. [J. Clin. Pharmacol., 1978, 26, 12, 570–574]; or in a proportion of 60% when administration is carried out during a meal: Weil et al. [Drug Metabolism, 1980, 18, 1, 115–120].

However, the use of sunflower oil as solvent requires excessively large volumes, of the order of 5 ml, which does not make possible formulation in a capsule with a volume which is suitable for and acceptable to patients.

Fenofibrate is a lipophilic molecule with the empirical formula $C_{20}O_4H_{21}Cl$ and the molecular weight 360 g. The white crystalline powder, of melting point 80° C., is virtually insoluble in water (8 mg/litre). Fenofibrate crystals have a size of between 10 and 150 $\mu$m.

The usual fatty solvents, such as the mono-, di- and triglycerides of $C_8$ to $C_{16}$ fatty acids derived from vegetable oils, have not made it possible to obtain the required fenofibrate solubilities. The addition of surfactants, such as polyglycosylated glycerides, substantially improves the solubilities, however.

The subject of the present invention is a new fenofibrate formulation, useful in particular in the treatment of hypercholesterolaemias and hypertriglyceridaemias, characterized in that it essentially contains fenofibrate in solution in a solubilizing agent consisting of a non-ionic surfactant, diethylene glycol monoethyl ether (DGME).

The selection of a surfactant solvent, such as diethylene glycol monoethyl ether (DGME) of molecular weight 134 g and of formula $C_2H_5$—O—$CH_2$—$CH_2$—O—$CH_2$—$CH_2$—OH, surprisingly makes it possible to obtain the desired results, namely complete dissolution of the fenofibrate, the consequence of which is a significant increase in the bioavailability of the fenofibrate, when administered orally, because its complete dissolution in DGME makes it possible to obtain virtually complete intestinal resorption.

DGME is a synthetic product obtained by condensation of ethylene oxide with ethanol and purified by rectification.

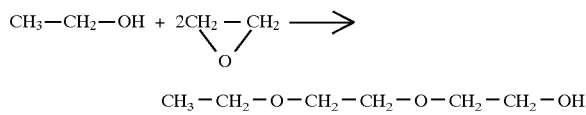

$$CH_3-CH_2-O-CH_2-CH_2-O-CH_2-CH_2-OH$$

It is oxidizable in air and must be stored under an inert atmosphere or in the presence of antioxidants, such as ascorbic acid, BHT or BHA.

DGME is a clear amphiphilic liquid of low viscosity which is soluble in water and partially soluble in vegetable oils. It is nontoxic and represents an ideal excipient for molecules which have little solubility in water. Its powerful solubilization action on lipophilic molecules is markedly greater than that of propylene glycol, glycerol or conventional polyethylene glycols such as PEG 200, 300, 400 and the like.

According to an advantageous embodiment of the fenofibrate solution, the solubilizing agent/fenofibrate ratio by weight is between 10 and 20.

According to another advantageous embodiment of the fenofibrate solution, it additionally comprises additives capable of increasing the solubilizing power of DGME and/or of increasing the stability of the said solution.

Another subject of the present invention is a process for the solubilization of fenofibrate, characterized in that it comprises the incorporation of fenofibrate particles with a size of less than 10 μm in a solubilizing agent consisting of a non-ionic surfactant, diethylene glycol monoethyl ether (DGME). The solubilizing agent/fenofibrate ratio by weight is preferably between 10 and 20.

Another subject of the present invention is a pharmaceutical composition intended for oral administration, characterized in that it contains an effective amount of a fenofibrate solution as defined above enclosed in a soft capsule, preferably a soft gelatin capsule.

Such a composition does indeed make it possible to reduce the dose of fenofibrate administered and to increase the intestinal absorption of fenofibrate.

Another subject of the present invention is a process for the preparation of a therapeutic composition containing fenofibrate in solution in diethylene glycol monoethyl ether (DGME) and presented in a soft capsule, which process is characterized in that it comprises:

the micronization of the fenofibrate, so as to obtain a powder in which the particles have a homogeneous size of less than 10 μm and preferably of the order of 7 to 10 μm, mixing the said powder with a DGME solution, until the fenofibrate has completely dissolved, and the incorporation of the fenofibrate solution in soft capsules.

Another subject of the present invention is the use of diethylene glycol monoethyl ether (DGME) as solubilization agent for fenofibrate.

An additional subject of the present invention is a process for improving the bioavailability of fenofibrate, characterized in that it comprises dissolving fenofibrate in diethylene glycol monoethyl ether (DGME).

In addition to the preceding arrangements, the invention additionally comprises other arrangements, which will emerge from the description which will follow, which refers to examples of the implementation of the process which is the subject of the present invention and to the appended drawing, in which:

Figure 1:
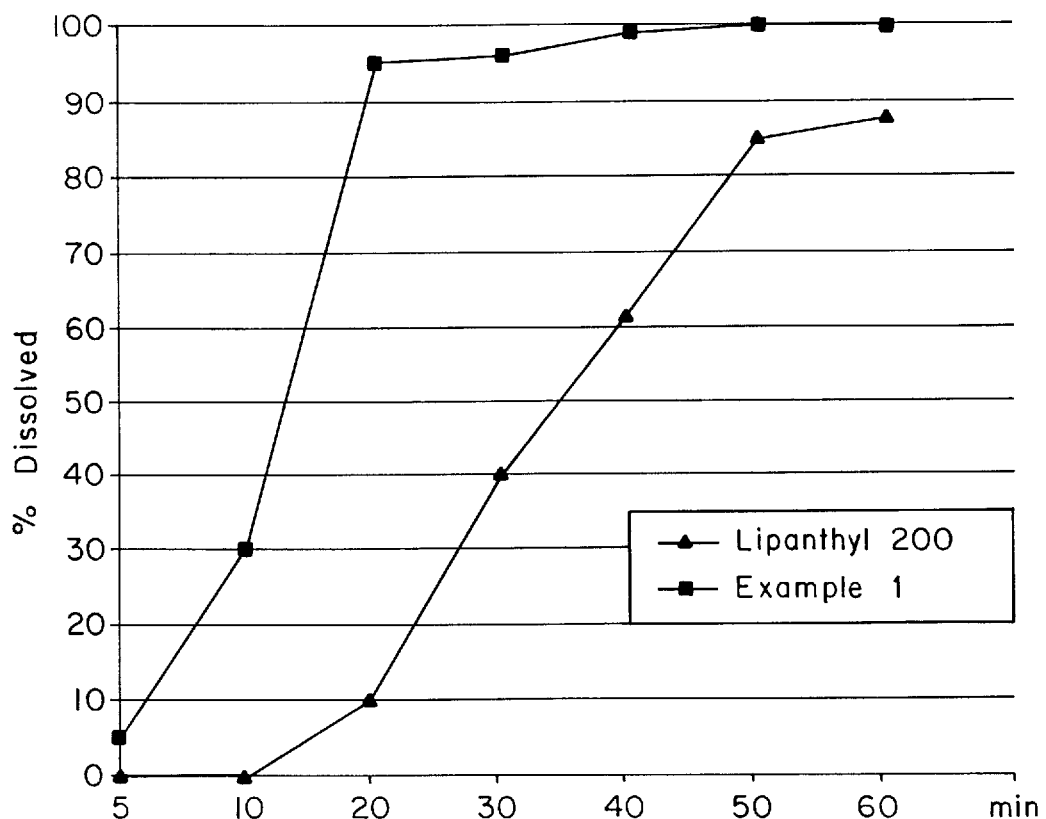
FIG. 1 illustrates a comparative study of the dissolution of fenofibrate with a composition according to the invention compared with Lipanthyl 200. This figure contains the time in minutes on the abscissa and the percentage of dissolved fenofibrate on the ordinate.

However, it must be clearly understood that these examples are given solely by way of illustration of the subject of the invention, of which they do not in any way constitute a limitation.

EXAMPLE 1

Preparation of Soft Capsules Containing 50 mg of Fenofibrate in Solution in DGME.

The amount of solvent used, per 100,000 soft gelatin capsules containing 50 mg of fenofibrate, is as follows:

| | |
|---|---|
| fenofibrate | 5.0 mg |
| DGME | 74 kg (or 75.0 liters of relative density 0.989) |

The fenofibrate is micronized in an air jet device so as to obtain a powder in which the particles have a homogeneous size of the order of 7 to 10 microns, in order for dissolution to take place rapidly and within a constant time period after mixing with the DGME. A clear and non-viscous solution is obtained which constitutes the medicinal solution. The soft capsules are then manufactured by the conventional process by injection of the medicinal solution and welding of the two halves of the capsule simultaneously.

The soft capsules contain 50 mg of fenofibrate dissolved in 0.75 ml of DGME. The solution encapsulated in transparent capsules is completely translucent.

Water-miscible glycol additives, as well as antioxidants, can be included in the proposed formula in order to substantially increase the solubilizing power of the DGME and to ensure the stability of the composition.

The unit dose of fenofibrate contained in each capsule can be between 30 and 200 mg.

EXAMPLE 2

Dissolution Study on the Soft Capsules According to Example 1.

A dissolution study, carried out according to the paddle dissolution method described in the European Pharmacopoeia, 2 Ed., "V 5.4. Dissolution test on solid oral forms", under the following conditions:

| | |
|---|---|
| nature of the dissolution medium: sodium lauryl sulphate | 0.1 M |
| volume | 1,000 ml |
| rotational speed | 50 rpm |
| temperature of the dissolution medium | 37° C. ± 0.5° C. |
| samples | 7 ml |
| quantitative determination by UV spectrophotometry at 290 nm | |

UV spectrophotometry at 290 nm showed the dissolution characteristics to be as follows:

| Dissolution time (in min) | % Dissolved Lipanthyl 200 ® | % Dissolved Example 1 |
|---|---|---|
| 5 | 0 | 5 |
| 10 | 0 | 30 |
| 20 | 10 | 95 |
| 30 | 40 | 96 |
| 40 | 62 | 99 |
| 50 | 65 | 100 |
| 60 | 88 | 100 |

The results are also illustrated in FIG. 1.

The administration of 3 successive doses of 50, 100 and 150 mg of fenofibrate to 6 healthy fasting volunteers made it possible to ascertain that the pharmacokinetics of fenofibric acid, the circulating metabolite of fenofibrate, were independent of the dose within the range of doses studied. This preliminary study shows that the administration of 100 mg of fenofibrate in a soft capsule according to the invention, taken as a single dose, results in a maximum plasma concentration within the concentration limits regarded as active according to Drouin et al. [Current Therapeutic Research, 1979, 26, 3, 357–362].

The maximum levels are reached 5 hours after administration and the elimination half-lives are of the order of 20 to 22 hours. The conventional pharmacokinetic parameters of fenofibrate are therefore unchanged.

However, the superbioavailability of fenofibrate obtained with the composition according to the invention makes it possible to obtain a significant improvement in the bioavailability of fenofibrate when compared with the compositions which are currently available.

The medicament which is the subject of the invention thus allows a decrease in the daily dose administered. In addition, the soluble presentation shows a more uniform intestinal absorption, resulting in a decrease in the variability of the blood levels between and within patients.

Consequently, the new soluble fenofibrate pharmaceutical dosage formulation results in an outstanding medicament which is easier to use and in which the side effects related to its use are reduced. The new formulation makes it possible to improve the comfort, the observance and the compliance of the patient.

In addition, in contrast to fenofibrate administered in the form of a powder, the administration of a soft capsule is not affected by the presence or absence of food in the stomach. The use of DGME, a water-miscible solvent, enables mixing to take place with the gastric juices and results in the absorbing intestinal mucous membranes becoming coated, which promotes the absorption of the active principle.

As the above has shown, the invention is in no way limited to those of its modes of use, of implementation and of application which have just been described more explicitly; on the contrary, it encompasses all the alternative forms thereof which may come to the mind of the expert in this field, without departing from the scope or from the context of the present invention.

I claim:

1. Fenofibrate pharmaceutical dosage formulation, characterized in that it essentially contains fenofibrate in solution in a solubilizing agent consisting of a non-ionic surfactant, diethylene glycol monoethyl ether (DGME).

2. Fenofibrate pharmaceutical dosage formulation according to claim 1, characterized in that the solubilizing agent/fenofibrate ratio by weight is between 10 and 20.

3. Fenofibrate pharmaceutical dosage formulation according to claim 1, characterized in that it additionally comprises additives capable of increasing the solubilizing power of DGME and/or of increasing the stability of the said solution.

4. Pharmaceutical composition intended for oral administration, characterized in that it contains an effective amount of a fenofibrate pharmaceutical dosage formulation according to claim 1 enclosed in a soft capsule.

5. Process for the preparation of a therapeutic composition according to claim 4, characterized in that it comprises:

micronization of the fenofibrate, so as to obtain a powder in which the particles have a homogeneous size of less than about 10 μm, mixing the said powder with a DGME solution until the fenofibrate has substantially completely dissolved, and incorporating the fenofibrate solution into said soft capsules.

6. Process for the solubilization of fenofibrate, characterized in that it comprises the incorporation of fenofibrate particles with a size of less than 10 μm in a solubilizing agent consisting of a non-ionic surfactant, diethylene glycol monoethyl ether (DGME).

7. Solubilization process according to claim 6, characterized in that the solubilizing agent/fenofibrate ratio by weight is between 10 and 20.

8. A method of solubilizing fenofibrate which comprises admixing said fenofibrate with diethylene glycol monoethyl ether.

9. Process for improving the bioavailability of fenofibrate, characterized in that it comprises dissolving fenofibrate in diethylene glycol monoethyl ether (DGME).

10. The composition as claimed in claim 4 wherein said soft capsules are comprised of gelatin.

11. The process as claimed in claim 5 wherein said micronization comminutes said fenofibrate to a particle size of about 7 to 10 μm.

12. The method as claimed in claim 8 which comprises admixing said fenofibrate in powder form with said diethylene glycol monoethyl ether until said fenofibrate completely dissolves in said ether.

* * * * *